United States Patent [19]

Kinugawa et al.

[11] Patent Number: 5,585,488

[45] Date of Patent: Dec. 17, 1996

[54] PROCESS FOR PRODUCING INDOLOCARBAZOLE DERIVATIVES

[75] Inventors: Masahiko Kinugawa; Yoshiaki Masuda, both of Sakai; Yukiteru Mimura, Shizuoka; Chikara Murakata, Hachioji; Hiromitsu Saito, Kawasaki; Takehiro Ogasa, Sakai; Masaji Kasai, Fujisawa; Shinji Tomioka, Hashimoto, all of Japan

[73] Assignee: Kyowa Hakko Kogyo Co., Ltd., Tokyo, Japan

[21] Appl. No.: 601,033

[22] PCT Filed: Jun. 30, 1995

[86] PCT No.: PCT/JP95/01309

§ 371 Date: Feb. 23, 1996

§ 102(e) Date: Feb. 23, 1996

[87] PCT Pub. No.: WO96/01263

PCT Pub. Date: Jan. 18, 1996

[30] Foreign Application Priority Data

Jul. 4, 1994 [JP] Japan .................... 6-152103

[51] Int. Cl.[6] .............................. C07D 498/22
[52] U.S. Cl. .................... 540/545; 540/546; 540/487
[58] Field of Search .................... 540/545, 546, 540/487

[56] References Cited

U.S. PATENT DOCUMENTS

| | | | |
|---|---|---|---|
| 5,013,854 | 5/1991 | Bunnell | 549/496 |
| 5,084,568 | 1/1992 | Bunnell | 540/487 |
| 5,344,926 | 9/1994 | Murakata et al. | 540/545 |

FOREIGN PATENT DOCUMENTS 155284  7/1987  Japan .

OTHER PUBLICATIONS

Bioorganic & Medicinal Chem. Letters, vol. 4, No. 11 (Jun. 1994) 1333–38.

*Primary Examiner*—Mukund J. Shah
*Assistant Examiner*—Pavanaram K. Sripada
*Attorney, Agent, or Firm*—Fitzpatrick, Cella, Harper & Scinto

[57] ABSTRACT

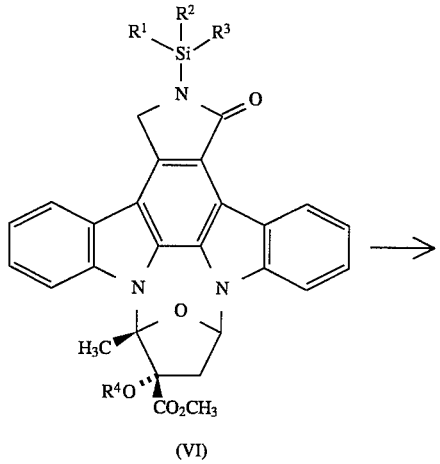

(VI)

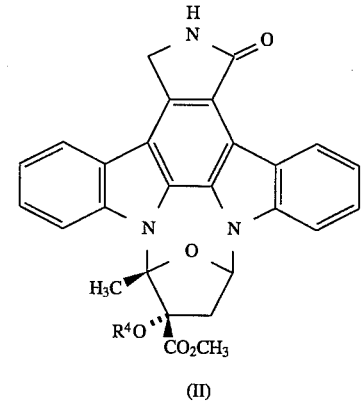

(II)

In the formulae, $R^1$, $R^2$, and $R^3$ independently represent lower alkyl or aryl, and $R^4$ represents lower alkyl.

The present invention relates to a process for producing an indolocarbazole derivative represented by Formula (II), comprising the acidic treatment of a silylated indolocarbazole derivative represented by Formula (VI).

3 Claims, No Drawings

PROCESS FOR PRODUCING INDOLOCARBAZOLE DERIVATIVES

TECHNICAL FIELD

The present invention relates to an industrial process for selectively and efficiently producing indolocarbazole derivatives which have protein kinase C-inhibiting activity.

BACKGROUND ART

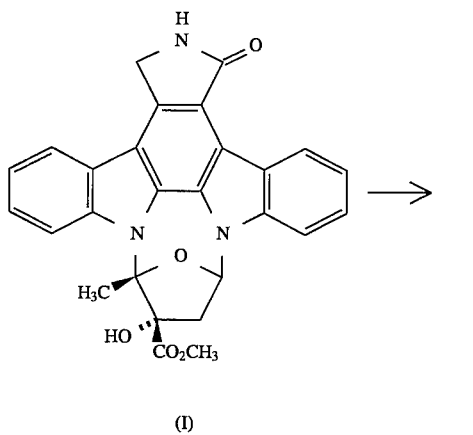

(I)

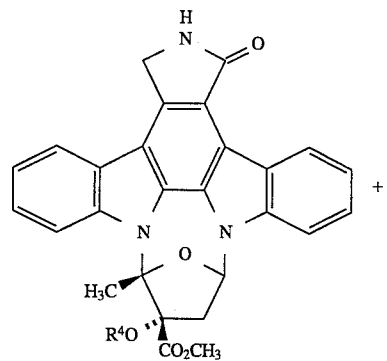

(II)

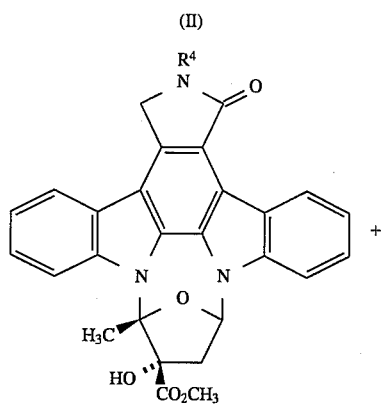

(III)

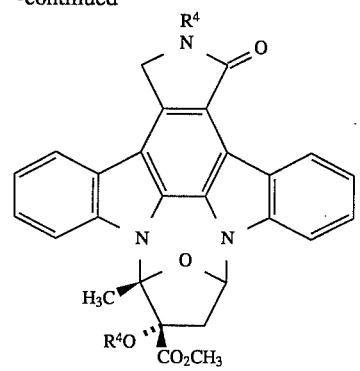

(IV)

In the formulae, $R^4$ represents lower alkyl.

Hereinafter, compounds represented by Formula (I), Formula (II), Formula (III), and Formula (IV) are referred to as Compound (I), Compound (II), Compound (III), and Compound (IV), respectively. The same applies to the compounds of other formula numbers.

It is known that Compound (II) has protein kinase C-inhibiting activity, and the process for producing Compound (II) as shown above is disclosed in Japanese Published Unexamined Patent Application No. 155284/87. According to the process, Compound (II) is directly produced from Compound (I). However, in the process, Compound (III) wherein a nitrogen atom in the amide group is lower-alkylated, and Compound (IV) wherein both of a hydroxyl group and a nitrogen atom in the amide group are lower-alkylated are produced in large quantities as by-products at the same time. Thus, the yield of the desired Compound (II) is low, and a complicated technique unsuitable for mass production, such as silica gel chromatography, is required for purification.

DISCLOSURE OF THE INVENTION

The present invention relates to a process for producing an indolocarbazole derivative represented by Formula (II), comprising: selective silylation of a nitrogen atom in the amide group of Compound (I) for obtaining a compound represented by Formula (V):

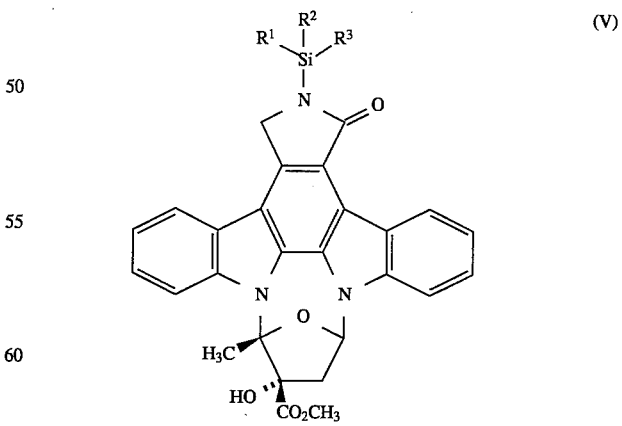

(V)

wherein $R^1$, $R^2$, and $R^3$ independently represent lower alkyl or aryl; lower-alkylation of Compound (V) to obtain a silylated indolocarbazole derivative represented by Formula (VI):

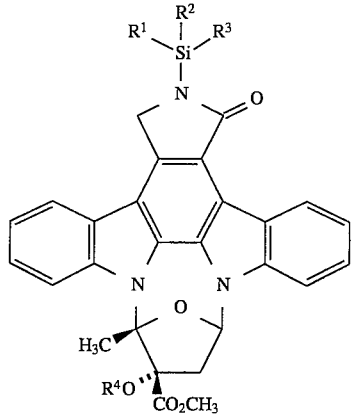

(VI)

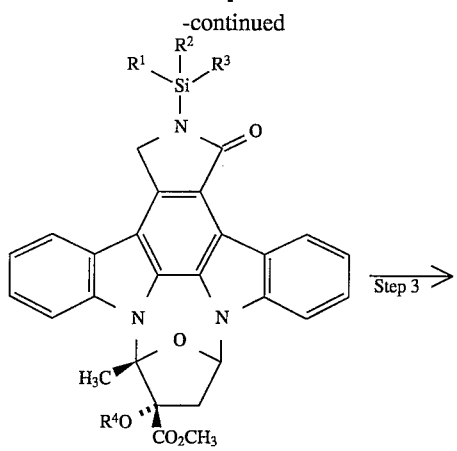

wherein R¹, R², R³, and R⁴ have the same meanings as defined above; and the acidic treatment of the silylated indolocarbazole derivative.

In addition, the present invention provides a silylated indolocarbazole derivative represented by Formula (VI).

In the definitions of the groups in Formula (I) to Formula (VI), the lower alkyl means a straight-chain or branched alkyl group having 1 to 6 carbon atoms such as methyl, ethyl, propyl, isopropyl, butyl, sec-butyl, tert-butyl pentyl, isopentyl, neopentyl, and hexyl. The aryl means a group such as phenyl and naphtyl.

The process of the present invention is described in detail below.

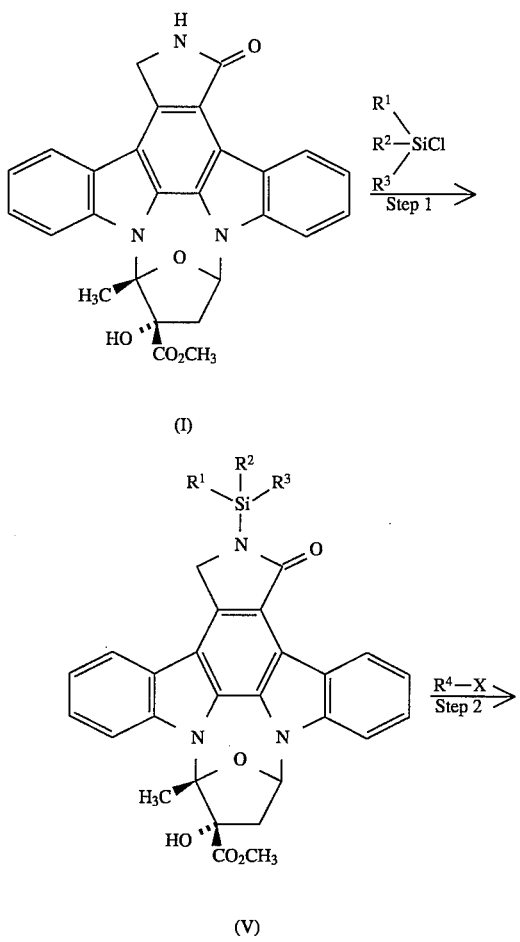

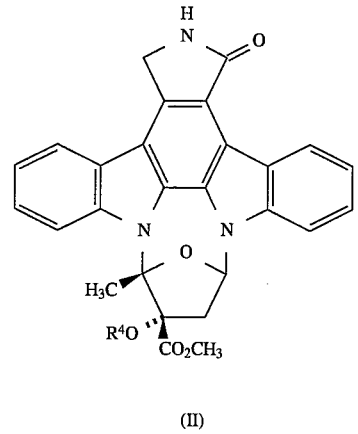

(II)

In the formulae, X represents halogen, and R¹, R², R³, and R⁴ have the same meanings as defined above.

The halogen means chlorine, bromine, or iodine.

The starting Compound (I) can be obtained according to the method described in Japanese Published Unexamined Patent Application No. 41489/85.

Step 1

Compound (V) can be obtained by reacting Compound (I) with 1 to 20 equivalents of tri-substituted silyl chloride in the presence of 1 to 20 equivalents of a base such as triethylamine, pyridine and imidazole, in a solvent at −30° to 50° C. for 0.5 to 24 hours. As a solvent, a halogenated hydrocarbon such as methylene chloride, chloroform, ethylene dichloride and carbon tetrachloride, an ester such as ethyl acetate, isopropyl acetate, tert-butyl acetate, isobutyl acetate and butyl acetate, and dimethylformamide are used singly or in combination in an amount of 1 to 50-fold (by weight) based on Compound (I).

Step 2

Compound (VI) can be obtained by reacting Compound (V) with 1 to 20 equivalents of alkyl halide in the presence of 1 to 20 equivalents of a base such as lithium hydroxide, potassium hydroxide, sodium hydroxide and sodium hydride, in a solvent at −30° to 50° C. for 0.5 to 24 hours. As a solvent, dimethylformamide and dimethylsulfoxide are used singly or in combination in an amount of 1 to 50-fold (by weight) based on Compound (V).

Step 3

Compound (II) can be obtained by treating Compound (VI) with 1 to 100 equivalents of hydrochloric acid, sulfuric acid, acetic acid, hydrobromic acid, trifluoroacetic acid, methane sulfonic acid, or the like, in a solvent or without a solvent. As a solvent, an alcohol such as methanol, ethanol and isopropanol, acetone, and acetonitrile are used singly or in combination in an amount of 1 to 100-fold (by weight) based on Compound (VI). The reaction is carried out at −30° C. to the boiling temperature of the employed solvent for 0.5 to 24 hours.

The intermediates and the desired compounds in the process described above can be easily isolated and purified by subjecting them to a post-treatment conventionally used in organic synthetic chemistry such as extraction, washing, drying and concentration, followed by crystallization and filtration. The intermediates may also be subjected to the subsequent reaction without purification, after the reaction or after the post-treatment.

Compound (II) obtained as described above has protein kinase C-inhibiting activity (Japanese Published Unexamined Patent Application No. 155284/87).

Examples and Comparative Example are described below.

The physicochemical data of each compound were determined by the following apparatus.

Melting point: Mettler FR61

MS: Hitachi M-80B (determined by SIMS method)

$^1$H-NMR: Nippon Bruker AC-300 (300 MHz)

IR: Shimadzu FTIR-4300 (determined by KBr method)

BEST MODE FOR CARRYING OUT THE INVENTION

EXAMPLE 1

Methyl 9α, 10β, 12α-2-(tert-butyldimethylsilyl)-2, 3, 9, 10, 11, 12-hexahydro-10-hydroxy-9-methyl-1-oxo-9, 12-epoxy-1H-diindolo[1,2,3-fg:3',2',1'-kl]pyrrolo-[3,4-i][1,6]benzodiazocine-10-carboxylate [Compound (V-1)]

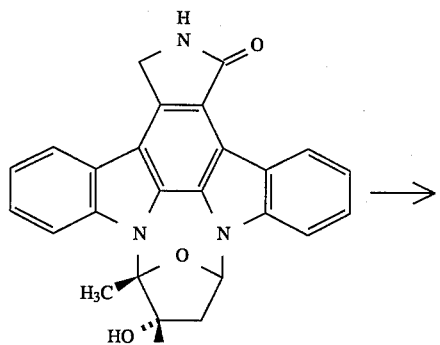

(I)

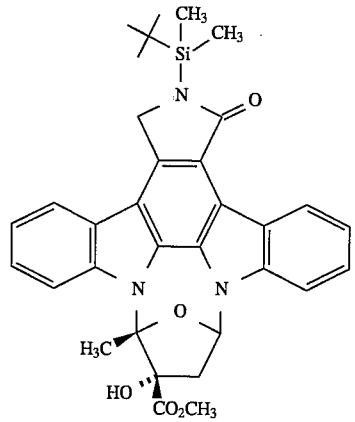

(V-1)

Ethyl acetate (800 ml), dimethylformamide (50 ml), and triethylamine (45.0 ml, 321 mmol) were added to methyl 9α, 10β, 12α-2-3,9,10,11,12-hexahydro-10-hydroxy-9-methyl-1-oxo-9,12-epoxy-1H-diindolo[1,2,3-fg:3',2',1'-kl]pyrrolo [3,4-i][1,6]benzodiazocine-10-carboxylate [Compound (I)] (50.0 g, 107 mmol), and a solution of tert-butyldimethylsilylylchloride (48.3 g, 321 mmol) dissolved in ethyl acetate (200 ml) was added thereto at room temperature, followed by stirring for 5 hours while maintaining the temperature in a range of 25° to 35° C. After partition of the reaction mixture by adding 1000 ml of water, the organic layer was washed twice with 1000 ml of a saturated aqueous solution of sodium chloride and dried over anhydrous sodium sulfate. The desiccating agent was filtered off, the solvent was distilled off under reduced pressure, and 600 ml of methanol was added to the residue, followed by stirring for 30 minutes at room temperature. After adding 150 ml of water, the mixture was stirred again for 30 minutes. Stirring was further continued for 5 hours under ice-cooling. The precipitated solid was collected by filtration and the solvent was distilled off by drying under reduced pressure to give 51.7 g (89.0 mmol, yield 83.2%) of the title compound.

Melting Point: 235°–241° C. (decomposition)

MS (m/z): 582 (M$^+$+1)

$^1$H-NMR(300 MHz,DMSO-d$_6$) δ(ppm): 9.25(1H, d,J=8.0 Hz), 8.17 (1H,d,J=7.7 Hz), 7.99(1H, d,J=8.5 Hz), 7.95(1H, d, J=8.3 Hz), 7.54(2H,t,J=7.3 Hz), 7.42(1H, t,J=7.3 Hz), 7.34(1H, t,J=7.6 Hz), 7.20(1H,t,J=5.1 Hz), 6.44(1H, s), 5.15(2H, d,j=4.7 Hz), 3.97(3H,s), 3.21(1H, d, J=5.0 Hz), 2.20(3H,s), 2.05(1H, dd, J=13.8,4.5 Hz), 1.08(9H,s), 0.58(6H,s)

IR (KBr) v (cm$^{-1}$): 1746, 1670, 1585, 1458, 1347, 1275, 1202

EXAMPLE 2

Methyl 9α, 10β, 12α-2,3,9,10,11,12-hexahydro-10-hydroxy-9-methyl-1-oxo-2-triethylsilyl-9,12-epoxy-1H-diindolo-[1,2,3-fg:3',2',1'-kl]pyrrolo[3,4-i][1,6]-benzodiazocine-10-carboxylate [Compound (V-2)]

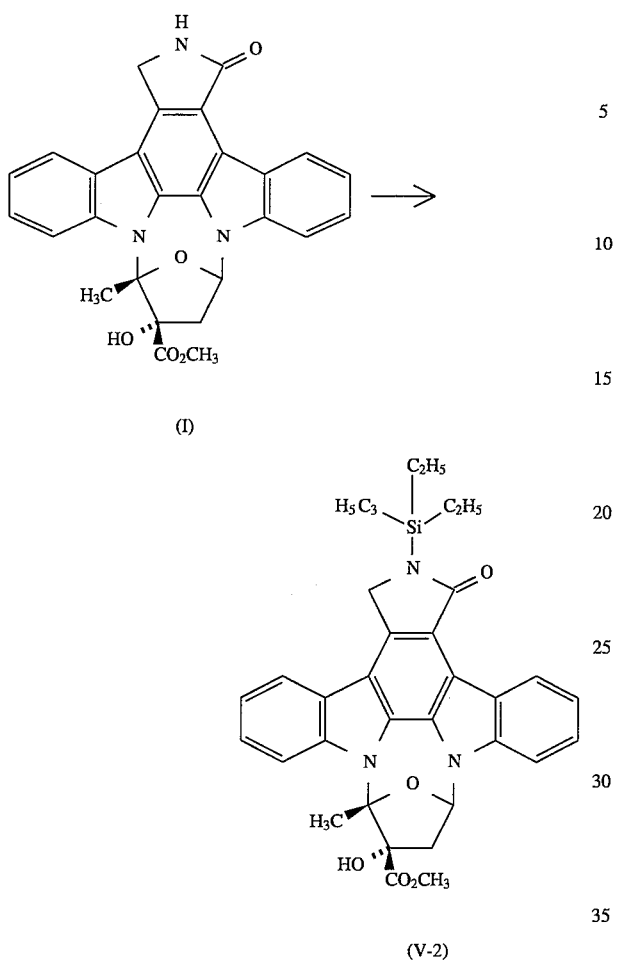

(I)

(V-2)

Ethyl acetate (10 ml), dimethylformamide (0.5 ml), and triethylamine (0.45 ml, 3.21 mmol) were added to Compound (I) (500 mg, 1.07 mmol), and triethylsilylchloride (0.54 ml, 3.22 mmol) was added thereto at room temperature, followed by stirring for 5 hours and 20 minutes while maintaining the temperature in a range of 25° to 35° C. After partition of the reaction mixture by adding 10 ml of water, the organic layer was washed twice with 10 ml of a saturated aqueous solution of sodium chloride and dried over anhydrous magnesium sulfate. The desiccating agent was filtered off, the solvent was distilled off under reduced pressure, and the residue was subjected to column chromatography on 10 g of silica gel (chloroform:ethyl acetate=5:1). After evaporation of the solvent under reduced pressure, 10 ml of hexane was added to the residue, followed by stirring for 5 hours under ice-cooling. The precipitated solid was collected by filtration and the solvent was distilled off by drying under reduced pressure to give 437 mg (0.752 mmol, yield 70%) of the title compound.

Melting Point: 155°–158° C. (decomposition)

MS (m/z): 582 (M$^+$+1)

$^1$H-NMR(300MHz,CDCl$_3$) δ(ppm): 9.39(1H,d,J=8.0 Hz), 7.96 (1H,d,J=7.5 Hz), 7.78(1H,d,J=8.4 Hz), 7.49(2H, d, J=3.5 Hz), 7.45(1H, dd, J=8.3,1.1 Hz), 7.37(1H, t, J=7.5 Hz), 7.34(1H, dt,J=8.1,4.0 Hz), 6.92(1H, dd, J=7.3,4.9 Hz), 5.02(2H,s), 4.09(3H,s), 3.67(1H,s), 3.25(1H, dd, J=14.3,7.4 Hz), 2.25(1H,dd, J=14.3, 4.9 Hz), 2.23(3H,s), 1.2–1.0(15H,m)

IR(KBr) v(cm$^{-1}$): 1732, 1668, 1587, 1456, 1132, 743

EXAMPLE 3

Methyl 9α,10β,12α-2,3,9,10,11,12-hexahydro-10-hydroxy-9-methyl-1-oxo-2-triphenylsilyl-9,12-epoxy-1H-diindolo-[1,2,3,-fg:3',2',1'-kl]pyrrolo[3,4-i][1,6]-benzodiazocine-10-carboxylate [Compound (V-3)]

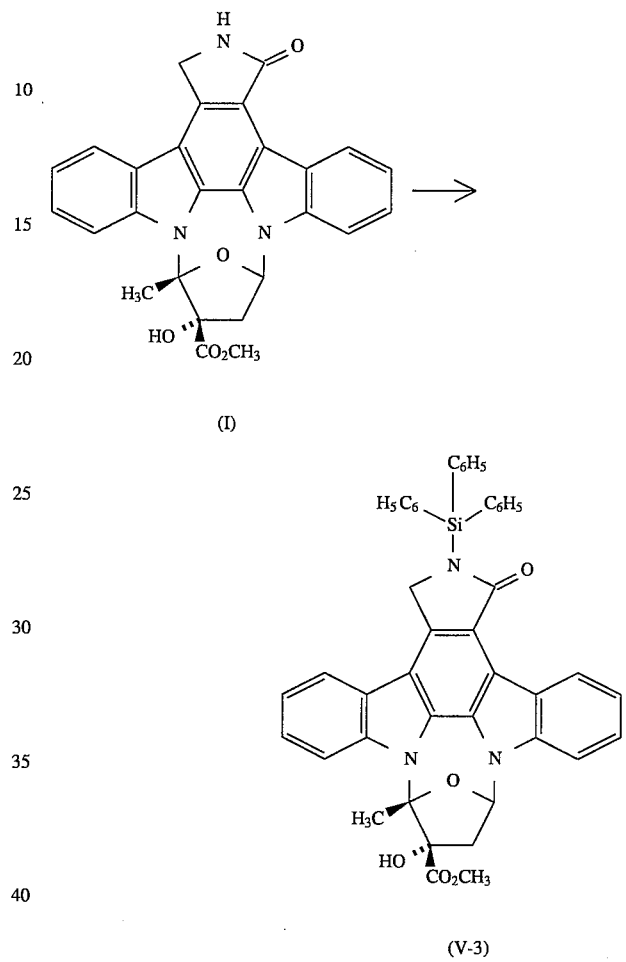

(I)

(V-3)

Ethyl acetate (8.0 ml), dimethylformamide (0.5 ml), and triethylamine (0.45 ml, 3.21 mmol) were added to Compound (I) (500 mg, 1.07 mmol), and a solution of triphenylsilylchloride (947 mg, 3.21 mmol) dissolved in ethyl acetate (2.0 ml ) was added thereto at room temperature, followed by stirring for 5 hours while maintaining the temperature in a range of 25° to 35° C. After partition of the reaction mixture by adding 10 ml of water, the organic layer was washed twice with 10 ml of a saturated aqueous solution of sodium chloride and dried over anhydrous magnesium sulfate. The desiccating agent was filtered off, the solvent was distilled off under reduced pressure, and 6.0 ml of methanol was added to the residue, followed by stirring for 30 minutes at room temperature. Stirring was further continued for 5 hours under ice-cooling. The precipitated solid was collected by filtration and the solvent was distilled off by drying under reduced pressure to give 689 mg (0.949 mmol, yield 88.7%) of the title compound.

Melting Point: 218°–222° C. (decomposition)

MS (m/z): 726(M$^+$+1)

$^1$H-NMR(300 MHz,CDCl$_3$) δ(ppm): 9.37(1H, d,J=8.0 Hz), 7.9–7.7 (6H,m), 7.74 (1H, d,J=7.7 Hz), 7.56(1H, d,J=7.7 Hz), 7.5–7.3(12H,m), 7.3–7.2(2H,m), 6.90(1H, dd, J=7.2, 4.9 Hz), 4.90 (2H,s), 4.07 (3H, s), 3.69

(1H,s), 3.24 (1H,dd,J=14.3,7.4 Hz), 2.24 (1H,dd, J=14.3,4.9 Hz), 2.20 (3H,s)

IR (KBr) v (cm⁻¹): 1732, 1668, 1587, 1456, 1132, 743

EXAMPLE 4

Methyl 9α, 10β, 12α-2,3,9,10,11,12-hexahydro-10-hydroxy-9-methyl-1-oxo-2-triisopropylsilyl-9,12-epoxy-1H-diindolo[1,2,3-fg:3',2',1'-kl]pyrrolo[3,4-i][1,6]-benzodiazocine-10-carboxylate [Compound (V-4)]

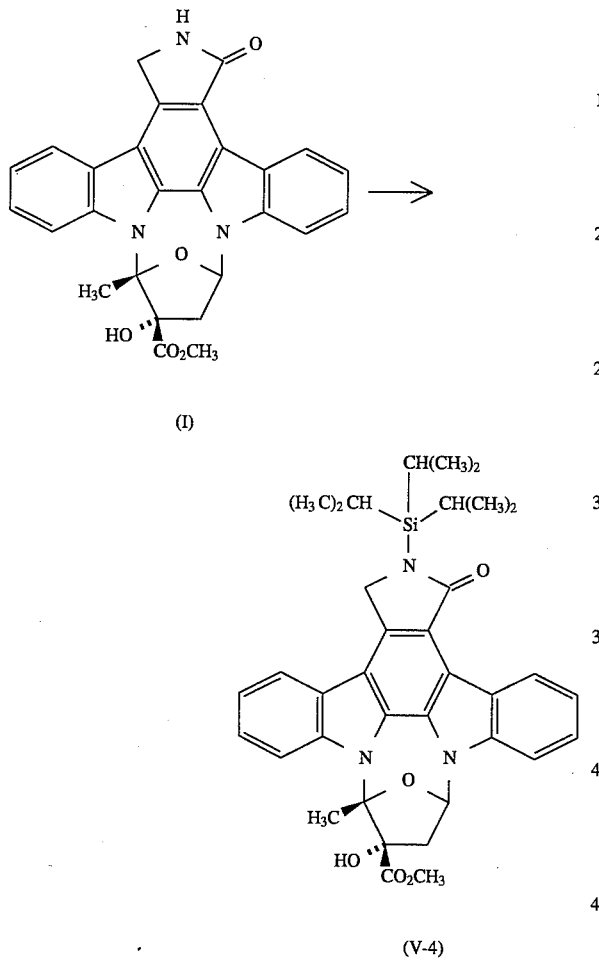

Ethyl acetate (10 ml), dimethylformamide (1.4 ml), and triethylamine (0.9 ml, 6.44 mmol) were added to Compound (I) (500 mg, 1.07 mmol), and triisopropylsilylchloride (1.38 ml, 6.45 mmol) was added thereto at room temperature, followed by stirring for 24 hours while maintaining the temperature in a range of 25° to 35° C. After partition of the reaction mixture by adding 10 ml of water, the organic layer was washed twice with 10 ml of a saturated aqueous solution of sodium chloride and dried over anhydrous sodium sulfate. The desiccating agent was filtered off, the solvent was distilled off under reduced pressure, and the residue was subjected to column chromatography on 20 g of silica gel (hexane:ethyl acetate=2:1). After evaporation of the solvent under reduced pressure, 18 ml of hexane was added to the residue, and the mixture was stirred for 30 minutes at room temperature and further stirred for 5 hours under ice-cooling. The precipitated solid was collected by filtration and the solvent was distilled off by drying under reduced pressure to give 572 mg (0.917 mmol, yield 85.7%) of the title compound.

Melting Point: 230°–234° C. (decomposition)

MS (m/z): 624 (M⁺+1)

¹H-NMR(300 MHz,CDCl₃) δ(ppm): 9.41 (1H,d,J=8.0 Hz), 7.96 (1H,d,J=6.8 Hz), 7.78 (1H, d,J=8.3 Hz), 7.49 (2H, d, J=3.7 Hz), 7.45(1H, dd, J=8.3,1.1 Hz), 7.38(1H, t, J=7.1 Hz), 7.34(1H,dt,J=8.0,4.0 Hz), 6.92(1H, dd, J=7.3,4.6 Hz), 5.12(2H,s), 3.97(3H,s), 3.25 (1H, dd, J=14.6,7.3 Hz), 2.25(1H, dd, J=14.3,4.9 Hz), 2.22 (3H,s), 1.79(3H,dt,J=15.2,7.6 Hz), 1.27(18H, d, J=7.5 Hz)

IR (KBr) v(cm⁻¹): 1747, 1670, 1587, 1458, 1365, 1276, 1200, 744

EXAMPLE 5

Methyl 9α,10β,12α-2-(tert-butyldiphenylsilyl)-2,3,9,10,11,12-hexahydro-10-hydroxy-9-methyl-1-oxo-9, 12-epoxy-1H-diindolo[1,2,3-fg:3',2',1'-kl]pyrrolo-[3,4-i][1,6]benzodiazocine -10-carboxylate [Compound (V-5)]

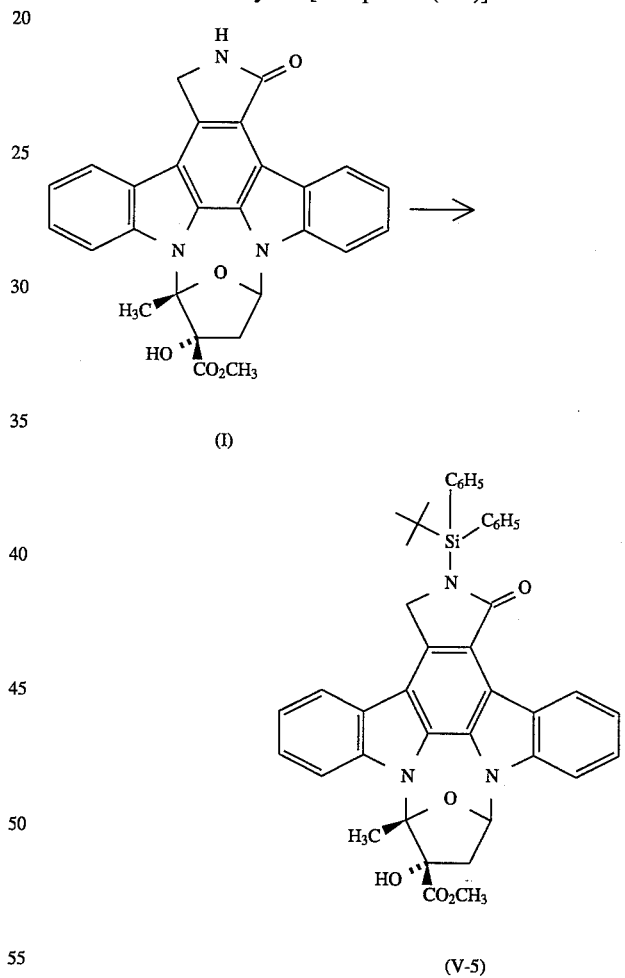

Ethyl acetate (10 ml), dimethylformamide (0.5 ml), and triethylamine (1.35 ml, 9.69 mmol) were added to Compound (I) (500 mg, 1.07 mmol), and tert-butyldiphenylsilylchloride (2.52 ml, 9.69 mmol) was added thereto at room temperature, followed by stirring for 24 hours while maintaining the temperature at 50° C. After partition of the reaction mixture by adding 10 ml of water, the organic layer was washed twice with 10 ml of a saturated aqueous solution of sodium chloride and dried over anhydrous sodium sulfate. The desiccating agent was filtered off, the solvent was distilled off under reduced pressure, and the residue was subjected to column chromatography on 80 g of silica gel (hexane:ethyl acetate=2:1). After evaporation of the solvent at reduced pressure, 10 ml of hexane was added to the residue, and the mixture was stirred for 30 minutes at room temperature and further stirred for 5 hours under ice-cooling. The precipitated solid was collected by filtration and the solvent was distilled off by drying under reduced pressure to give 572 mg (0.587 mmol, yield 54.9%) of the title compound.

Melting Point: 186°–198° C. (decomposition)

MS (m/z): 706 (M$^+$+1)

$^1$H-NMR(300 MHz,CDCl$_3$) δ(ppm): 9.44 (1H,d,J=8.0 Hz), 7.8–7.7(4H,m), 7.5–7.3 (11H,m), 7.21 (1H, t,J=7.4 Hz), 6.92(1H, dd, J=7.2,5.2 Hz), 4.76(2H,s), 4.09(3H,s), 3.66(1H,s), 3.25(1H,dd, J=14.3,7.4 Hz), 2.25(1H, dd, J=14.3, 4.9 Hz), 2.20 (3H,s), 1.42 (9H,s)

IR (KBr) v(cm$^{-1}$): 1733, 1676, 1587, 1458, 1111, 741

EXAMPLE 6

Methyl 9α,10β,12α-2- (tert-butyldimethylsilyl)-2,3,9,10,11,12-hexahydro-10-methoxy-9-methyl-1-oxo-9,12-epoxy-1H-diindolo[1,2,3-fg:3',2',1'-kl]pyrrolo-[3,4-i][1,6]benzodiazocine-10-carboxylate [Compound (VI-1)]

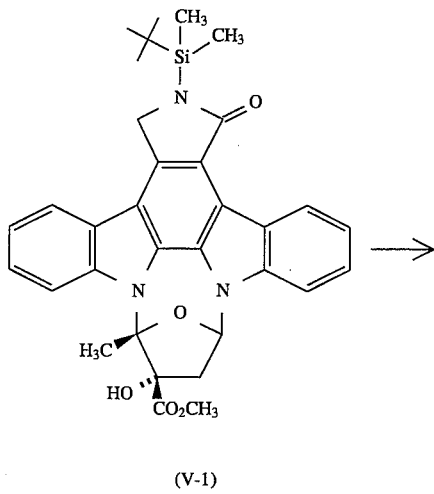

(V-1)

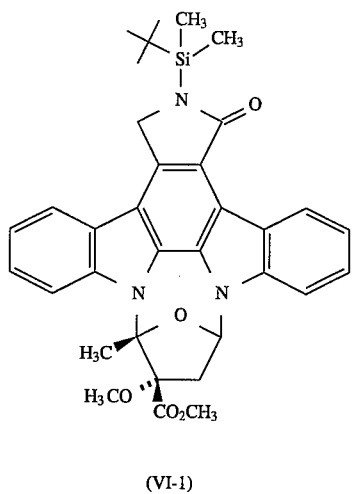

(VI-1)

Under nitrogen atmosphere, 1000 ml of dimethylformamide and 16.5 ml (258 mmol) of methyl iodide were added to 50.0 g (86.1 mmol) of Compound (V-1) obtained in Example 1, and 2.05 g (86.1 mmol) of lithium hydroxide was added thereto at room temperature, followed by stirring for one hour while maintaining the temperature in a range of 20° to 30° C. Then, 2.05 g (86.1 mmol) of lithium hydroxide was added to the mixture and the mixture was stirred for one hour while maintaining the temperature in a range of 20° to 30° C. Further, 2.05 g (86.1 mmol) of lithium hydroxide was added to the mixture and the mixture was stirred for 3 hours while maintaining the temperature in a range of 20° to 30° C. For partition, the reaction mixture was added to a cooled mixture of 1250 ml of ethyl acetate, 1000 ml of water, 25.0 g of citric acid, and 50.0 g of sodium chloride. After extraction of the aqueous layer with 500 ml of ethyl acetate, the organic layer was combined, washed once with 500 ml of water and twice with 500 ml of a saturated aqueous solution of sodium chloride, and dried over anhydrous sodium sulfate. The desiccating agent was filtered off, the solvent was distilled off under reduced pressure, and 1000 ml of acetonitrile was added to the residue, followed by stirring for 30 minutes at room temperature. After ice-cooling, 100 ml of water was added thereto, and the mixture was further stirred for 3 hours under ice-cooling. The precipitated solid was collected by filtration and the solvent was distilled off by drying under reduced pressure to give 46.4 g (78.0 mmol, yield 90.6%) of the title compound.

Melting Point: 260°–272° C. (decomposition)

MS (m/z): 596(M$^+$+1)

$^1$H-NMR(300 MHz,DMSO-d$_6$) δ(ppm):9.23(1H, d,J=8.1 Hz), 8.13 (1H, d,J=7.7 Hz), 7.98(1H, d,J=8.2 Hz), 7.89(1H, d, J=8.5 Hz), 7.53(2H,t,J=7.6 Hz), 7.40(1H, t,J=7.5 Hz), 7.33(1H,t,J=7.5 Hz), 7.28(1H,t,J=7.5 Hz), 5.14(2H, s), 4.01(3H,s), 3.54(1H, dd, J=13.7,7.5 Hz), 3.05(3H, s), 2.21(3H,s), 2.10(1H, dd, J=13.9,4.9 Hz), 1.07(9H, s), 0.56(6H,s)

IR(KBr) v(cm$^{-1}$): 1732, 1664, 1589, 1456, 1350, 1272, 1098

EXAMPLE 7

Methyl 9α,10β,12α-2,3,9,10,11,12-hexahydro-10-methoxy-9-methyl-1-oxo-2-triethylsilyl-9,12-epoxy1H--diindolo-[1,2,3-fg:3',2',1'-kl]pyrrolo[3,4-i][1,6]-benzodiazocine-10-carboxylate [Compound (VI-2)]

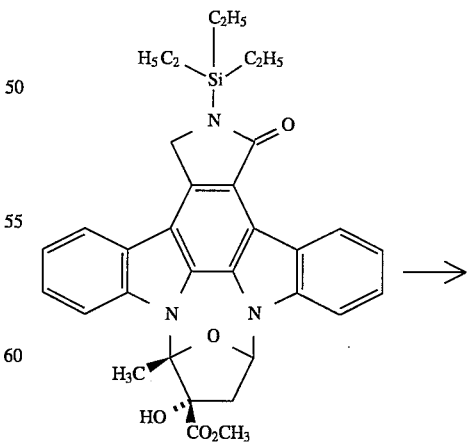

(V-2)

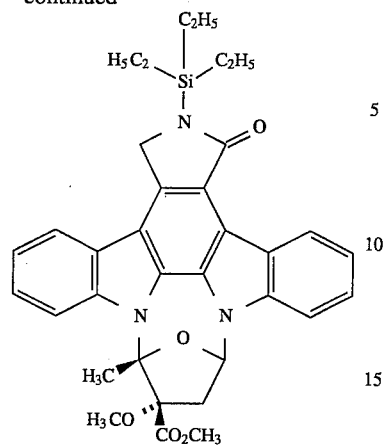

(VI-2)

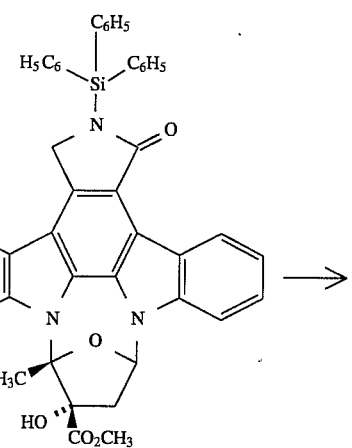

(V-3)

Under nitrogen atmosphere, 3.0 ml of dimethylformamide and 80 μl (1.29 mmol) of methyl iodide were added to 150 mg (0.258 mmol) of Compound (V-2) obtained in Example 2, and 31 mg (1.29 mmol) of lithium hydroxide was added thereto under ice-cooling, followed by stirring for 3.5 hours while maintaining the temperature below 5° C. The reaction mixture was added to 5.0 ml of ethyl acetate. After partition, the aqueous layer was extracted with 10 ml of ethyl acetate, and the organic layer was combined, washed once with 10 ml of water and twice with 10 ml of a saturated aqueous solution of sodium chloride, and dried over anhydrous sodium sulfate. The desiccating agent was filtered off, the solvent was distilled off under reduced pressure, and the residue was purified by column chromatography on 10 g of silica gel (hexane:ethyl acetate=3:1). The solvent was distilled off by drying under reduced pressure to give 23 mg (0.039 mmol, yield 15.0%) of the title compound.

Melting Point: 225°–228° C. (decomposition)

MS (m/z): 596 (M$^+$+1)

$^1$H-NMR(300 MHz,CDCl$_3$) δ(ppm): 9.38(1H, d,J=8.0 Hz), 7.94 (1H,d,J=7.2 Hz), 7.89(1H,d,J=8.4 Hz), 7.6–7.4(3H,m), 7.4–7.3(2H,m), 6.99(1H,dd, J=7.2,5.2 Hz), 5.02(2H, s), 4.04(3H,s), 3.36(1H, dd, J=13.7,7.3 Hz), 3.12(3H, s), 2.22(3H,s), 2.21(1H, dd, J=13.2,5.3 Hz), 1.2–1.0 (15H,m)

IR(KBr) ν(cm$^{-1}$): 1740, 1662, 1587, 1454, 1367, 1265, 1201, 1148, 1096, 741

EXAMPLE 8

Methyl 9α, 10β,12α-2,3,9,10,11,12-hexahydro-10-methoxy-9-methyl-1-oxo-2-triphenylsilyl-9,12-epoxy-1H-diindolo-[1,2,3-fg:3',2',1'-kl]pyrrolo[3,4-i][1,6]-benzodiazocine-10-carboxylate [Compound (VI-3)]

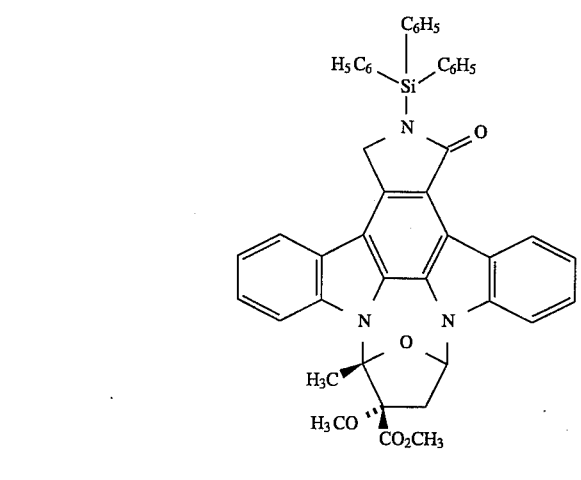

(VI-3)

Under nitrogen atmosphere, 6.0 ml of dimethylformamide and 0.13 ml (2.07 mmol) of methyl iodide were added to 300 mg (0.413 mmol) of Compound (V-3) obtained in Example 3, and 49 mg (2.07 mmol) of lithium hydroxide was added thereto at room temperature, followed by stirring for 50 minutes while maintaining the temperature in a range of 20° to 30° C. For partition, the reaction mixture was added to a cooled mixture of 7.5 ml of ethyl acetate, 6.0 ml of water, 163 mg of citric acid, and 240 mg of sodium chloride. After extraction of the aqueous layer with 5.0 ml of ethyl acetate, the organic layer was combined, washed once with 5.0 ml of water and twice with 5.0 ml of a saturated aqueous solution of sodium chloride, and dried over anhydrous magnesium sulfate. The desiccating agent was filtered off, the solvent was distilled off under reduced pressure, and the residue was purified by column chromatography on 15 g of silica gel (hexane:ethyl acetate=2:1). The solvent was distilled off by drying under reduced pressure to give 23 mg (0.032 mmol, yield 7.7%) of the title compound.

Melting Point: 222°–230 ° C. (decomposition)

MS (m/z): 740 (M$^+$+1)

$^1$H-NMR(300 MHz,CDCl$_3$) δ(ppm): 9.35(1H, d,J=8.0 Hz), 7.9–7.7(7H,m), 7.7–7.3(13H,m), 7.3–7.2(2H,m), 6.99(1H, dd, J=7.2, 5.2 Hz), 4.90 (2H,s), 4.03(3H,s), 3.37(1H, dd, J=13.3,7.3 Hz), 3.12(3H,s), 2.21(1H, dd, J=11.5, 7.0 Hz), 2.21 (3H,s)

IR(KBr) v(cm⁻¹): 1728, 1674, 1589, 1458, 1365, 1272, 1205, 1134, 1096, 746

EXAMPLE 9

Methyl 9α,10β,12α-2,3,9,10,11,12-hexahydro-10-methoxy-9-methyl-1-oxo-2-triisopropylsilyl-9,12-epoxy-1H-diindolo[1,2,3,-fg:3',2',1'-kl]pyrrolo[3,4-i][1,6]-benzodiazocine-10-carboxylate [Compound (VI-4)]

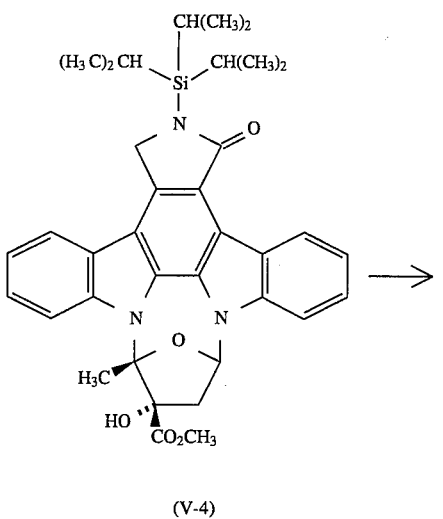

(V-4)

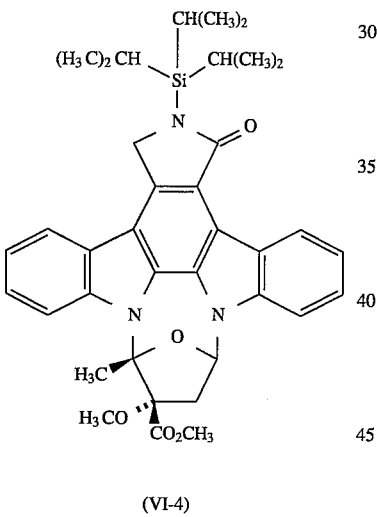

(VI-4)

Under nitrogen atmosphere, 3.0 ml of dimethylformamide and 90 μl (1.44 mmol) of methyl iodide were added to 150 mg (0.240 mmol) of Compound (V-4) obtained in Example 4, and 28 mg (1.16 mmol) of lithium hydroxide was added thereto under ice-cooling, followed by stirring for 4.5 hours while maintaining the temperature in a range of 0° to 5° C. For partition, the reaction mixture was added to a cooled mixture of 10 ml of ethyl acetate and a 0.5mM phosphate buffer (pH 5.9). After extraction of the aqueous layer with 10 ml of ethyl acetate, the organic layer was combined, washed once with 4.0 ml of water and three times with 4.0 ml of a saturated aqueous solution of sodium chloride, and dried over anhydrous magnesium sulfate. The desiccating agent was filtered off, the solvent was distilled off under reduced pressure, and the residue was purified by column chromatography on 10 g of silica gel (hexane:ethyl acetate=3:1). The solvent was distilled off by drying under reduced pressure to give 99 mg (0.155 mmol, yield 64.7%) of the title compound.

Melting Point: 272°–275° C. (decomposition)

MS (m/z): 638 (M⁺+1)

¹H-NMR (300 MHz, CDCl₃) δ(ppm): 9.40(1H, d,J=7.9 Hz), 7.94 (1H, d, J=7.4 Hz), 7.89(1H, d,J=8.4 Hz), 7.6–7.4(3H,m), 7.4–7.3(2H,m), 6.98(1H, dd, J=7.2,5.2 Hz), 5.12(2H, s), 4.11 (3H,s), 3.36(1H, dd, J=13.2, 7.3Hz), 3.12(3H, s), 2.22(3H,s), 2.21(1H, dd, J=13.2, 5.3 Hz), 1.79 (3H, dt, J=15.2,7.6 Hz), 1.27 (18H,d,J= 7.5 Hz)

IR (KBr) v(cm⁻¹): 1740, 1662, 1587, 1454, 1367, 1265, 1201, 1148, 1096, 741

EXAMPLE 10

Methyl 9α,10β,12α-2-(tert-butyldiphenylsilyl)-2,3,9,10,11,12-hexahydro-10-methoxy-9-methyl-1-oxo-9,12-epoxy-1H-diindolo[1,2,3-fg:3',2',1'-kl]pyrrolo-[3,4-i][1,6]benzodiazocine -10-carboxylate [Compound (VI-5)]

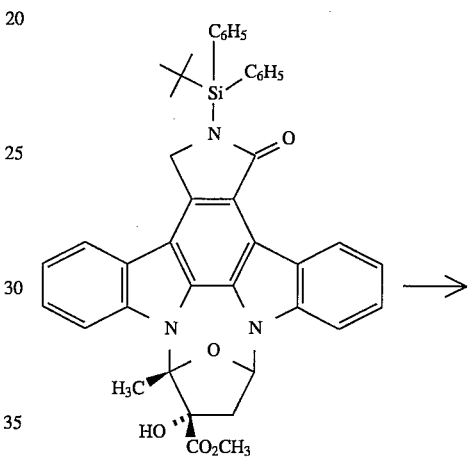

(V-5)

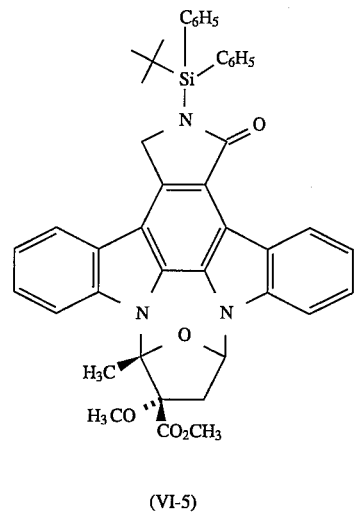

(VI-5)

Under nitrogen atmosphere, 3.0 ml of dimethylformamide and 66 μl (1.06 mmol) of methyl iodide were added to 150 mg (0.213 mmol) of Compound (V-5) obtained in Example 5, and 26 mg (1.09 mmol) of lithium hydroxide was added thereto at room temperature, followed by stirring for 3 hours while maintaining the temperature in a range of 20° to 30° C. For partition, the reaction mixture was added to a cooled mixture of 5 ml of ethyl acetate and 5 ml of a 0.5 mM phosphate buffer (pH 5.9). After extraction of the aqueous layer with 10 ml of ethyl acetate, the organic layer was combined, washed once with 10 ml of water and three times with 10 ml of a saturated aqueous solution of sodium chloride, and dried over anhydrous magnesium sulfate. The desiccating agent was filtered off, the solvent was distilled off under reduced pressure, and the residue was purified by column chromatography on 10 g of silica gel (hexane:ethyl acetate=3:1). The solvent was distilled off by drying under reduced pressure to give 148 mg (0.206 mmol, yield 96.5%) of the title compound.

Melting Point: 206°–209° C. (decomposition)

MS (m/z): 720 (M$^+$+1)

$^1$H-NMR(300 MHz,CDCl$_3$) δ(ppm): 9.43(1H,d,J=7.9 Hz), 7.84 (1H,d,J=8.4 Hz), 7.8–7.7(4H,m), 7.5–7.3(11H,m), 7.21(1H,t,J=7.5 Hz), 6.99(1H,dd, J=7.2,5.2 Hz), 4.76 (2H,s), 4.03 (3H,s), 3.37 (1H, dd, J=13.3,7.3 Hz), 3.13 (3H,s), 2.23(1H,dd, J=13.1,5.2 Hz), 2.20(3H,s), 1.42 (9H,s)

IR (KBr) v(cm$^{-1}$): 1736, 1676, 1587, 1458, 1342, 1269, 1143, 1114, 1096, 743

EXAMPLE 11

Methyl 9α,10β,12α-2,3,9,10,11,12-hexahydro-10-methoxy-9-methyl-1-oxo-9,12-epoxy-1H-diindolo[1,2,3-fg:3',2',1'-kl]pyrrolo[3,4-i][1,6]benzodiazocine-10-carboxylate [Compound (II-1)]

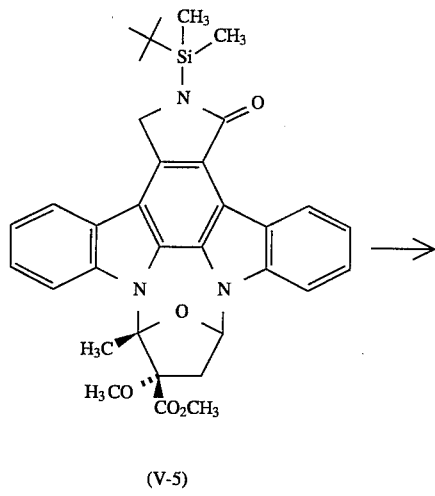

(V-5)

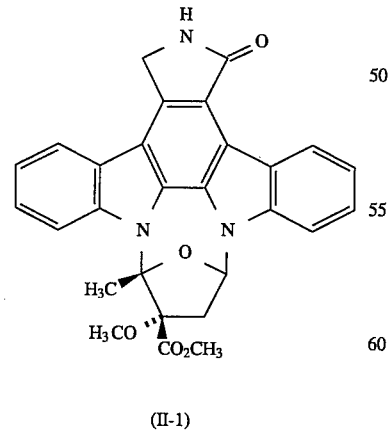

(II-1)

Isopropanol (1000 ml) was added to Compound (VI-1) (50.0 g, 84.0 mmol) obtained in Example 6, and 2N hydrochloric acid (100 ml) was added thereto at room temperature, followed by stirring for 3 hours while maintaining the temperature in a range of 70° to 80° C. After cooling, the mixture was further stirred for 3 hours under ice-cooling. The precipitated solid was collected by filtration and the solvent was distilled off by drying under reduced pressure to give 38.4 g [79.9 mmol, yield 95.1%, overall yield from Compound (I) 72%] of the title compound.

Melting Point: 252°–257° C. (decomposition)

MS (m/z): 482 (M$^+$+1)

$^1$H-NMR(300 MHz,DMSO-d$_6$) δ(ppm): 9.34 (1H, d,J= 7.8 Hz), 8.79 (1H,s), 8.16(1H,d,J=7.5 Hz), 8.08(1H, d,J=8.4 Hz), 7.99(1H, d,J=8.4 Hz), 7.62(2H,t,J=7.2 Hz), 7.48(1H,t, J=7.6 Hz), 7.42(1H,t,J=7.6 Hz), 7.39(1H,m), 5.13(2H, s), 4.10(3H,s), 3.64(1H,dd,J= 13.6,7.2 Hz), 3.15(3H, s), 2.30(3H,s), 2.20(1H, dd, J=13.6,5.0 Hz)

IR(KBr) v(cm$^{-1}$): 1735, 1680, 1460, 1395, 1315, 1272

EXAMPLE 12

Compound (II-1)

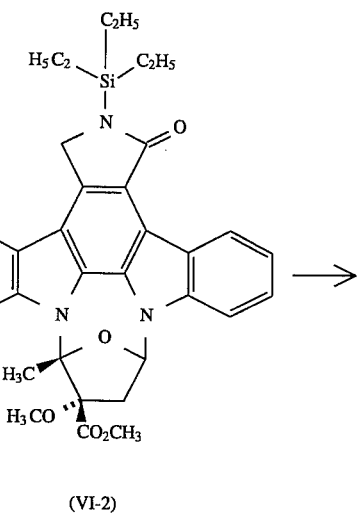

(VI-2)

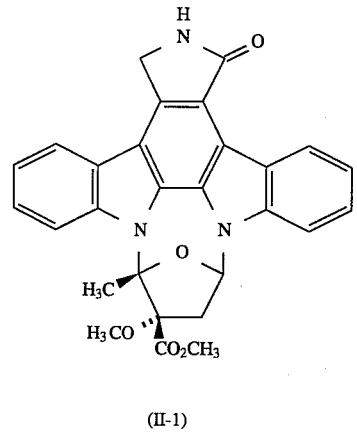

(II-1)

Ethanol (3.0 ml) was added to Compound (VI-2) (150 mg, 0.252 mmol) obtained in Example 7, and 2N hydrochloric acid (0.3 ml) was added thereto at room temperature, followed by stirring for 2.5 hours while maintaining the temperature at 30° C. After cooling, the mixture was further stirred for 2 hours under ice-cooling. The precipitated solid was collected by filtration and the solvent was distilled off by drying under reduced pressure to give 115 mg (0.239

EXAMPLE 13

Compound (II-1)

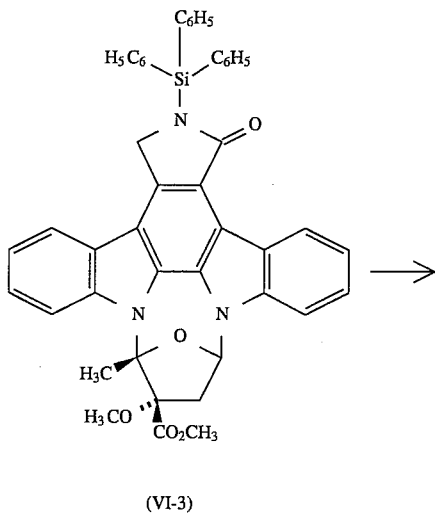

(VI-3)

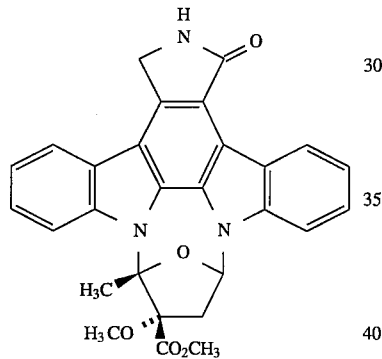

(II-1)

Ethanol (3.0 ml) was added to Compound (VI-3) (150 mg, 0.203 mmol) obtained in Example 8, and 2N hydrochloric acid (0.3 ml) was added thereto at room temperature, followed by stirring for 3 hours while maintaining the temperature in a range of 70° to 80° C. After cooling, the mixture was further stirred for 2 hours under ice-cooling. The precipitated solid was collected by filtration and the solvent was distilled off by drying under reduced pressure to give 89 mg (0.185 mmol, yield 91.2%) of the title compound. The compound obtained in this example exhibited mmol, yield 94.9%) of the title compound. The compound obtained in this example exhibited the same values of NMR, IR, and TLC as the compound obtained in Example 11.

the same values of NMR, IR, and TLC as the compound obtained in Example 11.

EXAMPLE 14

Compound (II-1)

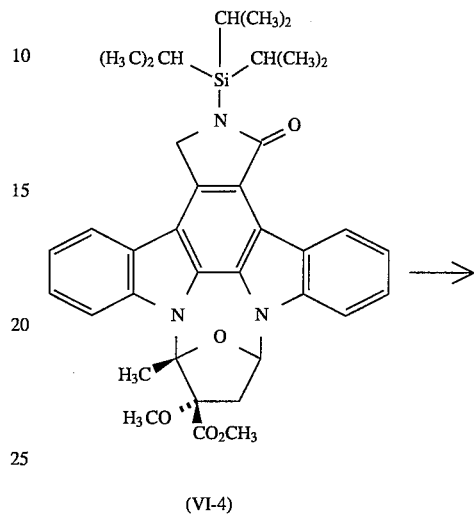

(VI-4)

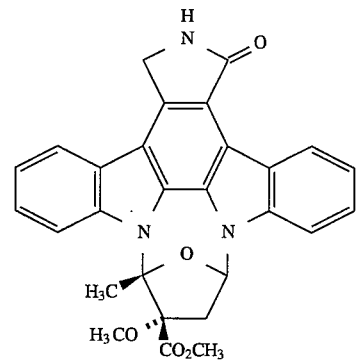

(II-1)

Ethanol (12.0 ml) was added to Compound (VI-4) (150 mg, 0.235 mmol) obtained in Example 9, and 2N hydrochloric acid (0.6 ml) was added thereto at room temperature, followed by stirring for 3 hours while maintaining the temperature in a range of 70° to 80° C. After cooling, the mixture was further stirred for 2 hours under ice-cooling. The precipitated solid was collected by filtration and the solvent was distilled off by drying under reduced pressure to give 90 mg (0.187 mmol, yield 79.6%) of the title compound. The compound obtained in this example exhibited the same values of NMR, IR, and TLC as the compound obtained in Example 11.

EXAMPLE 15

Compound (II-1)

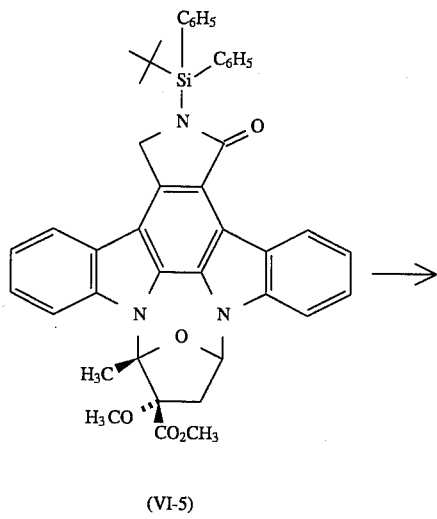

(VI-5)

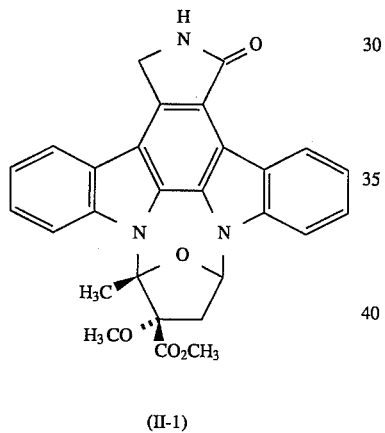

(II-1)

Ethanol (3.0 ml) was added to Compound (VI-5) (150 mg, 0.208 mmol) obtained in Example 10, and 2N hydrochloric acid (0.3 ml) was added thereto at room temperature, followed by stirring for 2.5 hours while maintaining the temperature at a range of 70° to 80° C. After cooling, the mixture was further stirred for 2 hours under ice-cooling. The precipitated solid was collected by filtration and the solvent was distilled off by drying under reduced pressure to give 91 mg (0.189 mmol, yield 90.8%) of the title compound. The compound obtained in this example exhibited the same values of NMR, IR, and TLC as the compound obtained in Example 11.

COMPARATIVE EXAMPLE 1

Compound (II-1)

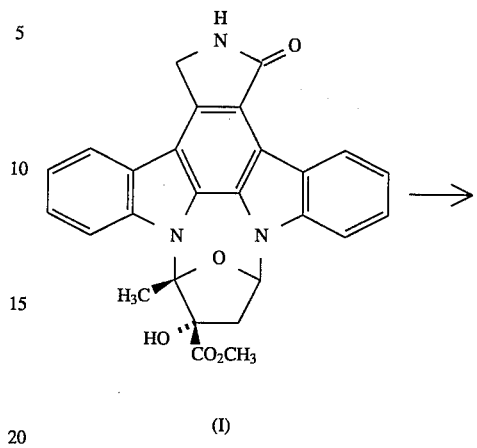

(I)

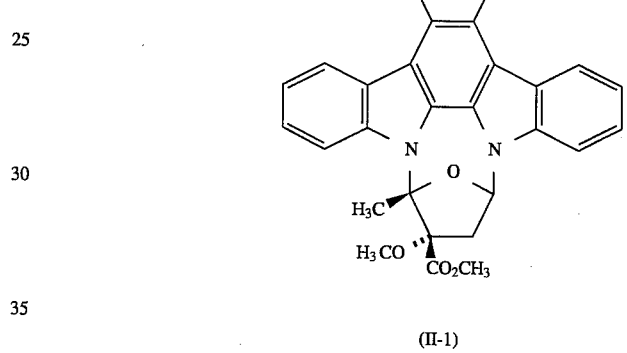

(II-1)

A solution (2 ml) of Compound (I) (184 mg, 0.4 mmol) in dimethylformamide was water-cooled and 50% sodium hydride in oil (19.2 mg, 0.4 mmol) was added thereto. After 20 minutes, 25 μl (0.4 mmol) of methyl iodide was added to the mixture, followed by stirring for one hour. Chloroform (20 ml) was added to the reaction mixture, and the solution was washed with water and dried over anhydrous sodium sulfate. The solvent was distilled off under reduced pressure, and the residue was purified by silica gel column chromatography (chloroform) to give 65 mg (0.14 mmol, yield 34%) of the title compound as a pale yellow powder.

Industrial Applicability

According to the present invention, there can be provided an industrial process for selectively and efficiently producing indolocarbazole derivatives which have protein kinase C-inhibiting activity.

We claim:

1. A process for producing an indolocarbazole derivative represented by Formula (II):

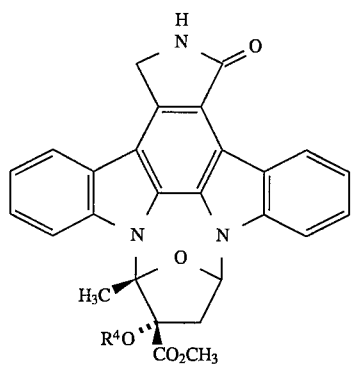

(II)

wherein R⁴ represents lower alkyl, comprising the acidic treatment of a silylated indolocarbazole derivative represented by Formula (VI):

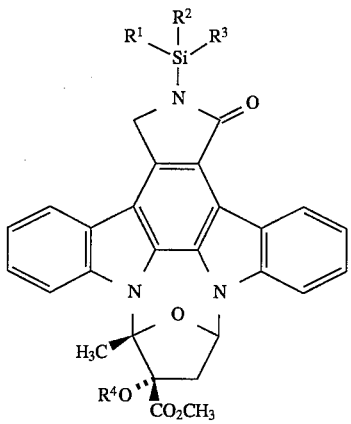

(VI)

wherein $R^1$, $R^2$, and $R^3$ independently represent lower alkyl or aryl, and $R^4$ has the same meaning as defined above.

2. A process for producing an indolocarbazole derivative represented by Formula (II) as set forth in claim 1, comprising: silylation of a compound represented by Formula (I):

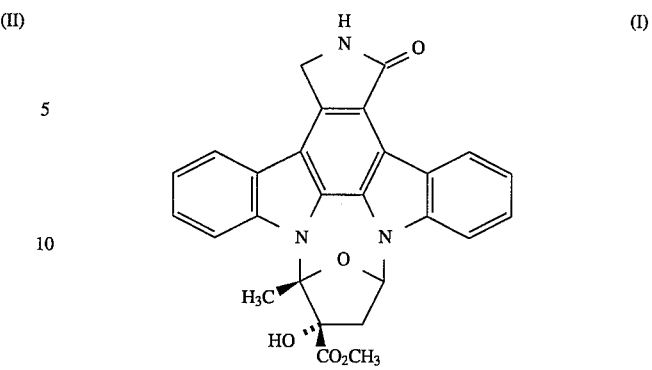

(I)

for obtaining a compound represented by Formula (V):

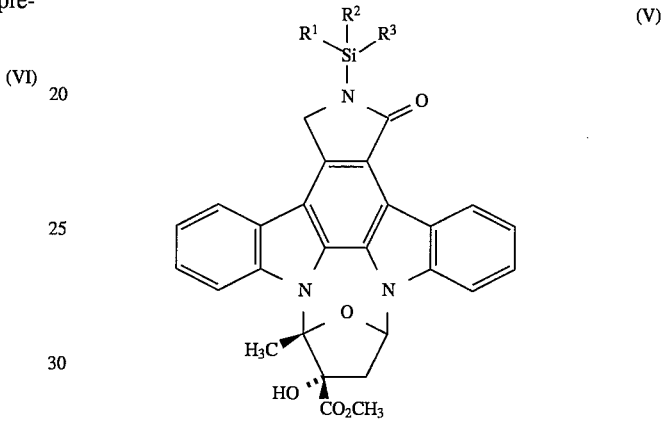

(V)

wherein $R^1$, $R^2$, and $R^3$ have the same meanings as defined above; lower-alkylation of the compound represented by Formula (V) to obtain a silylated indolocarbazole derivative represented by Formula (VI) as set forth in claim 1; and the acidic treatment of the silylated indolocarbazole derivative.

3. A silylated indolocarbazole derivative represented by Formula (VI) as set forth in claim 1.

* * * * *

UNITED STATES PATENT AND TRADEMARK OFFICE
CERTIFICATE OF CORRECTION

PATENT NO. : 5,585,488
DATED : December 17, 1996
INVENTOR(S) : Masahiko Kinugawa et al.

It is certified that error appears in the above-indentified patent and that said Letters Patent is hereby corrected as shown below:

COLUMN 7

Line 19, "$H_5C_3$" should read --$H_5C_2$--.

COLUMN 17

Line 47, "(V-5)" should read --(VI-1)--.

Signed and Sealed this

Tenth Day of June, 1997

Attest:

BRUCE LEHMAN

Attesting Officer

Commissioner of Patents and Trademarks